United States Patent
Gupta et al.

(12) 
(10) Patent No.: US 10,720,228 B2
(45) Date of Patent: Jul. 21, 2020

(54) METHOD AND SYSTEM FOR TESTING OF ACTIVE MOLECULES USING MOLECULAR SIMULATION OF SKIN MEMBRANE

(71) Applicant: Tata Consultancy Services Limited, Mumbai (IN)

(72) Inventors: Rakesh Gupta, Pune (IN); Balarama Sridhar Dwadasi, Pune (IN); Beena Rai, Pune (IN)

(73) Assignee: Tata Consultancy Services Limited, Mumbai (IN)

( * ) Notice: Subject to any disclaimer, the term of this patent is extended or adjusted under 35 U.S.C. 154(b) by 607 days.

(21) Appl. No.: 15/466,653

(22) Filed: Mar. 22, 2017

(65) Prior Publication Data

US 2017/0321349 A1    Nov. 9, 2017

(30) Foreign Application Priority Data

May 6, 2016   (IN) .............................. 201621015953

(51) Int. Cl.
| | |
|---|---|
| *G16B 35/00* | (2019.01) |
| *G16C 20/60* | (2019.01) |
| *G16C 20/30* | (2019.01) |
| *G16H 50/50* | (2018.01) |
| *G16C 10/00* | (2019.01) |
| *G16C 20/10* | (2019.01) |

(52) U.S. Cl.
CPC ............. *G16B 35/00* (2019.02); *G16C 20/30* (2019.02); *G16C 20/60* (2019.02); *G16H 50/50* (2018.01); *G16C 10/00* (2019.02); *G16C 20/10* (2019.02)

(58) Field of Classification Search
CPC ....................................................... G16B 35/00
USPC ............................................................ 702/19
See application file for complete search history.

(56) References Cited

PUBLICATIONS

Mathes, S.H., et al. "The use of skin models in drug development", Advanced Drug Delivery Reviews, vol. 69-70, pp. 61-102, Elsevier B.V., (2013).
Brohem, C.A.. et al., "Artificial skin in perspective: concepts and applications", vol. 24, pp. 35-50, John Wiley & Sons, (2010).
Shityakov, S , et al., "In silico predictive model to determine vector-mediated transport properties for the blood-brain barrier choline transporter", Advances and Applications in Bioinformatics and Chemistry, 7, pp. 23-26, Dovepress, (2014).

*Primary Examiner* — Jerry Lin
(74) *Attorney, Agent, or Firm* — Finnegan, Henderson, Farabow, Garrett & Dunner LLP (57) ABSTRACT

A system and method for testing of active molecules using simulation of skin membrane have been provided. The present disclosure provides a molecular level model of the skins upper protective layer Stratum-Corneum. The systems consist of a molecular model of the skins upper layer stratum corneum and permeate molecules. A protocol have been developed to perform molecular dynamics simulations which can be automated. The system predicts the permeability, partition coefficient and diffusivity of different active molecules like drugs and cosmetics through mentioned skin model using multiple molecule in single window constrained molecular dynamics simulations.

10 Claims, 12 Drawing Sheets

METHOD AND SYSTEM FOR TESTING OF ACTIVE MOLECULES USING MOLECULAR SIMULATION OF SKIN MEMBRANE

CROSS-REFERENCE TO RELATED APPLICATIONS AND PRIORITY

The present application claims priority from Indian non-provisional specification no. 201621015953 filed on 6 May 2016, the complete disclosure of which, in its entirety is herein incorporated by references.

TECHNICAL FIELD

The embodiments herein generally relates to the field of drug delivery and modelling of skin, and, more particularly, to a method and system for testing of active molecules such as biomolecules, nanoparticles, drugs etc. using molecular simulation of skin membrane.

BACKGROUND

Skin, the largest organ of our body protects us from the attack of foreign pathogens and provides barrier to the permeation of many harmful molecules and maintains the hydration level of tissues. The outer layer of skin, also known as Stratum Corneum (SC) is mainly responsible for these barrier properties.

The delivery of drugs through the skin provides a convenient route of administration because of high surface area of skin and can typically be self-administered. The accurate prediction of dermal uptake of chemicals is therefore relevant to both transdermal drug delivery as well as topical application of cosmetics. In recent past, transdermal delivery of small molecules (hydrophobic/hydrophilic drugs) and macromolecules (proteins, enzymes) has been an attractive as well as a challenging area of research. The transdermal route provides various advantages over conventional oral/intravenous routes. It allows lesser amount of drug to be administered thereby reducing its toxicity. Drugs with poor or less bio-availability can be delivered due to avoidance of the GI tract (a major barrier in oral route). This method provides pain free and easy administration and enhanced patience compliance.

The accurate prediction of dermal uptake of chemicals is relevant to both transdermal drug delivery as well as topical application of cosmetics. Extensive research has been carried out over the many years to predict the skin permeability of various drugs and cosmetic molecules. These efforts include experimental studies, development of theoretical models and empirical methods. The current industry standard, however, both in pharma and in cosmetics, is to conduct detailed in-vitro and in-vivo trials. These obviously incur huge expenses thereby leading to a very few successful candidates that are finally approved by regulatory authority (FDA). The 2-D in vitro cell culture studies do not accurately reflect the complex interactions that occur between the multiple cells present in the 3-D in vivo skin environment. In vivo studies in rodents and other small animals do not translate well to the human situation due to differences in anatomical structures. Though there are some commercially available human skin equivalents like EpiSkin (LOreal, Paris) and EpiDerm™ (MatTek, Massachusetts), these require highly specialized skills and are very expensive.

Further, the European Union (EU) regulation (76/768/EEC, February 2003) prohibits the use of animal or animal-derived substances for the development and testing of cosmetic and pharmaceutical ingredients. The fact that by 2008 only 20 transdermal drug formulations had been approved by FDA substantiates the challenges associated with their development.

Considering the time and costs involved in the development and testing of new drug/cosmetics formulations, it is imperative to supplement/replace some of the elaborate in-vivo/in-vitro tests with in-silico tests. A realistic in-silico model of human skin does not exist. Extensive research has been performed over the last several decades to predict skin permeability of various molecules. These efforts include the development of empirical approaches such as quantitative structure—permeability relationships and porous pathway theories as well as the establishment of rigorous structure-based models. However, a molecular-level understanding of the skin's surface layer—the Stratum Corneum (SC) which shall ultimately lead to the development of rapid in-silico screens to predict drug permeability from knowledge of its molecular structure alone is still not on the horizon. With the recent molecular level decoding of SC's structure, it is now possible to develop an appropriate virtual model to accurately mimic its barrier properties.

Molecular simulations offer a way to yield important physical insight and molecular level resolution with an ability to reproduce molecular and bulk properties. It has been recognized as an efficient and versatile technique for the study of biomolecules like bilayers, micelles and proteins. Various prior arts have focused on factorial design of experiments to screen drugs/cosmetics based on their permeability. Most of the simulation work till now involved only pure ceramide bilayer which is far from the real skin composition. Further, prior simulation work mostly focused on phospholipid cell membranes in liquid crystalline phase which makes sampling easier in molecular dynamic simulations. In addition to that, they only focused on the water permeability. The simulations till now have not been performed at physiological conditions and actual skin compositions.

SUMMARY

The following presents a simplified summary of some embodiments of the disclosure in order to provide a basic understanding of the embodiments. This summary is not an extensive overview of the embodiments. It is not intended to identify key/critical elements of the embodiments or to delineate the scope of the embodiments. Its sole purpose is to present some embodiments in a simplified form as a prelude to the more detailed description that is presented below.

In view of the foregoing, an embodiment herein provides a system for testing of active molecules using simulation of skin membrane. The system comprises a user interface, a memory and a processor. The user interface provides a structure library as a first input and a topology library as a second input. The processor is in communication with the memory. The processor comprises a model generation module, a simulation module, a diffusivity calculation module, a partition coefficient prediction module and a permeability prediction module. The model generation module generates a molecular model of the lipid matrix of the stratum corneum of the skin. The simulation module performs multiple molecules in a single window constrained molecular dynamics simulation on the active molecules using the molecular model of the stratum corneum of the skin. The diffusivity calculation module predicts diffusivity of the active molecules based on the simulation. The partition coefficient prediction module predicts partition coefficients of the active molecules based on the simulation. The permeability prediction module predicts permeability of the active molecules based on the simulation.

In another aspect, an embodiment provides a processor implemented method for testing of active molecules using simulation of skin membrane. Initially a structure library is prepared as a first input to the processor. A topology library is prepared as a second input to the processor. In the next step, an initial configuration is generated by the processor using the first input and the second input. Then, a molecular model of the stratum corneum of the skin is generated using the initial configuration. In the next step, multiple molecules in a single window constrained molecular dynamics simulation of the active molecules is performed using the molecular model of the stratum corneum of the skin. And finally the three parameters i.e., diffusivity, partition coefficients and permeability of active molecules are predicted based on the simulation.

In another embodiment, a non-transitory computer-readable medium having embodied thereon a computer program for testing of active molecules using simulation of skin membrane. Initially a structure library is prepared as a first input to the processor. A topology library is prepared as a second input to the processor. In the next step, an initial configuration is generated by the processor using the first input and the second input. Then, a molecular model of the stratum corneum of the skin is generated using the initial configuration. In the next step, multiple molecules in a single window constrained molecular dynamics simulation of the active molecules is performed using the molecular model of the stratum corneum of the skin. And finally the three parameters i.e., diffusivity, partition coefficients and permeability of active molecules are predicted based on the simulation.

It should be appreciated by those skilled in the art that any block diagram herein represent conceptual views of illustrative systems embodying the principles of the present subject matter. Similarly, it will be appreciated that any flow charts, flow diagrams, state transition diagrams, pseudo code, and the like represent various processes which may be substantially represented in computer readable medium and so executed by a computing device or processor, whether or not such computing device or processor is explicitly shown.

BRIEF DESCRIPTION OF THE DRAWINGS

The embodiments herein will be better understood from the following detailed description with reference to the drawings, in which.

The Figures depict various embodiments of the present invention for purposes of illustration only. One skilled in the art will readily recognize from the following discussion that alternative embodiments of the structures and methods illustrated herein may be employed without departing from the principles of the invention described herein.

DETAILED DESCRIPTION OF EMBODIMENTS

The embodiments herein and the various features and advantageous details thereof are explained more fully with reference to the non-limiting embodiments that are illustrated in the accompanying drawings and detailed in the following description. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Figure 1:
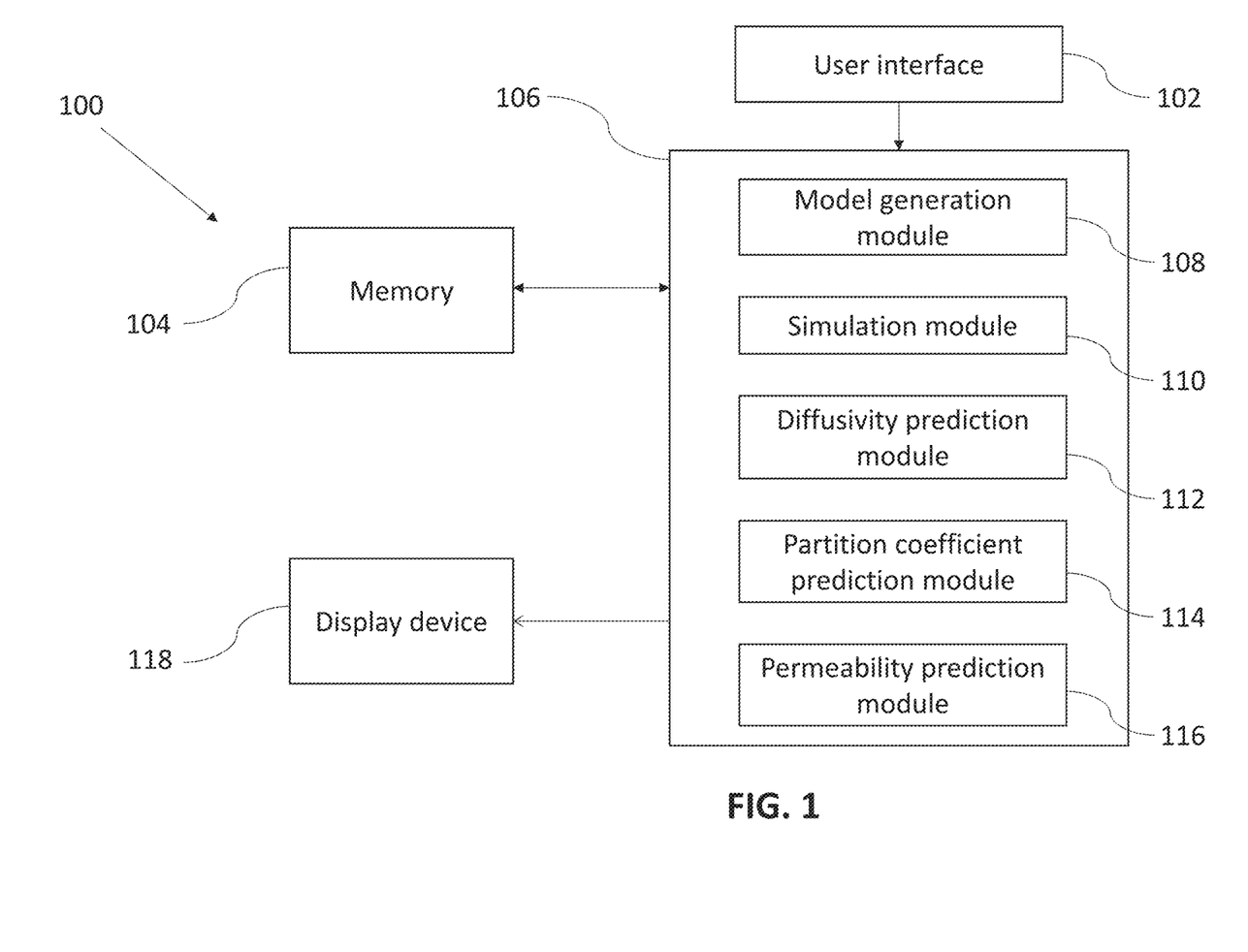
FIG. 1 illustrates a block diagram for testing of active molecules using simulation of skin membrane according to an embodiment of the present disclosure.

Referring now to the drawings, and more particularly to FIG. 1, where similar reference characters denote corresponding features consistently throughout the figures, there are shown preferred embodiments and these embodiments are described in the context of the following exemplary system and/or method.

Figure 2:
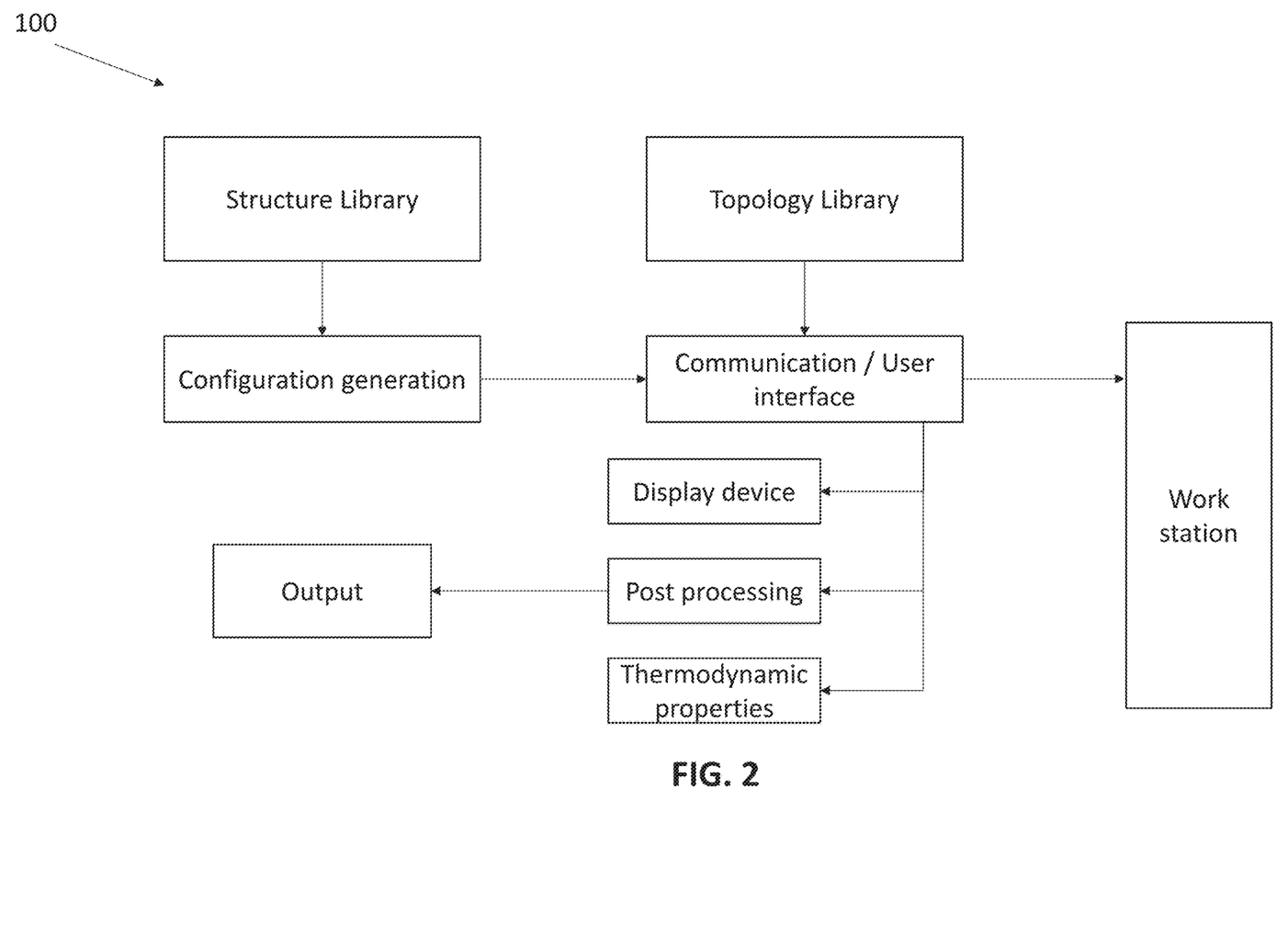
FIG. 2 illustrates an architectural workflow of the system according to an embodiment of the present disclosure.

According to an embodiment of the disclosure, a system 100 for testing of active molecules using simulation of skin membrane is shown in the block diagram of FIG. 1 and architectural workflow of FIG. 2. The system 100 provides a molecular modeling based approach to develop the complex skin model at atomistic level and further calculation of various parameters such as permeability, diffusivity, partition coefficients and free energy of permeation of molecules through it using constrained molecular dynamics simulations. The system 100 also configured for in-silica molecular processing, testing, and screening for simulating skin lipids membrane. The transport properties of small molecules across this virtual skin membrane are computed and compared with the experimental data. The model and methodology thus validated further could be used in the design and development of big and complex pharmaceuticals/cosmetics for virtual screening of the products. The system 100 provides a nano-scale level picture of active molecules permeation through skin lipids.

According to an embodiment of the disclosure, the system 100 may use a variety of active molecules like drugs and cosmetics. These active molecules provides nano-scale level picture through mentioned skin model using constrained molecular dynamics simulations. The active molecules may include proteins, drugs, polymers, nanoparticles etc. Though it should be appreciated that use of any other molecules for the testing in the system 100 is well within the scope of this disclosure. In various examples, transdermal delivery of small molecules (hydrophobic/hydrophilic drugs) and macromolecules (proteins, enzymes) has also been used.

According to an embodiment of the disclosure, the system 100 includes a user interface 102, a memory 104 and a processor 106 in communication with the memory 104 as shown in FIG. 1. The processor 106 configured to execute a plurality of algorithms stored in the memory 104. The processor 106 further includes a plurality of modules for performing various functions. The plurality of modules include a model generation module 108, simulation module 110, a diffusivity calculation module 112, a partition coefficient calculation module 114 and a permeability prediction module 116.

The user interface 102 is configured to provide the structure library as a first input and the topology library as a second input. The structure library may include skin lipids, stratum corneum components, biological molecules, proteins, drugs, polymers, nanoparticies, water, hydrophilic and hydrophobic molecules and solvents. The topology library includes force fields and individual molecule parameter files. The user interface 102 may include a variety of software and hardware interfaces, for example, a web interface, a graphical user interface, and the like. The I/O interface user may allow the system 100 to interact with the user directly or through the client devices. Further, the user interface 102 may enable the system 100 to communicate with other computing devices, such as web servers and external data servers (not shown). The user interface 102 can facilitate multiple communications within a wide variety of networks and protocol types, including wired networks, for example, LAN, cable, etc., and wireless networks, such as WLAN, cellular, or satellite. The user interface 102 may include one or more ports for connecting a number of devices including assistive technology devices or adaptive products used by people with disability to one another or to another server.

According to an embodiment of the disclosure, the model generation module 108 generates a molecular level model of the lipid matrix of the skin's upper protective layer stratum corneum. The skin model is made up of three most important components Ceramide, cholesterol and free fatty acid. The molecular model employs bonded and non-bonded parameters to describe the interaction between the molecules.

According to an embodiment of the disclosure, the simulation module 110 performs multiple molecules in a single window constrained molecular dynamics simulation on the active molecules using the molecular model of the stratum corneum of the skin. The constrained molecular dynamics simulations are performed under constant temperature and pressure condition. The constrained MD simulation results might be hindered by improper or inadequate sampling of whole bilayer phase space. The main challenge was in developing the initial structures of the bilayers with permeate at different constrained positions. The initial structures are prepared in such a way that in single simulation window multiple molecules (4 in current simulation) could be constrained. The minimum distances between the molecules in each window were kept at 1.2 nm to avoid the interaction between them, doing so each system mimic equivalent to four systems with single constrained molecule. The system 100 also reduces the simulation time required for the sampling of whole phase space by constraining multiple molecules in single window of the simulation.

The results from the constrained molecular dynamics simulation might be hindered by poor sampling of the phase space. To avoid this issue multiple (~200) and long (~25-30 ns) independent simulations are performed usually. In the present disclosure, the number of independent simulations have also been significantly reduced (~50) by generating initial structures with multiple constrained molecules. This method and approach saves computation time significantly and provides proper sampling of phase space. The protocol uses constrained molecular dynamics approach for the calculation of in plane and lateral diffusivity, partition coefficients, free energy and permeability.

According to an embodiment of the disclosure, the system 100 is configured to predict various parameters. The system predicts diffusivity of the active molecules based on the simulation using the diffusivity calculation module 112. The system 100 further predicts the partition coefficients of the active molecules based on the simulation the partition coefficient prediction module 114. The system 100 also predicts the permeability of the active molecules based on the simulation using the permeability prediction module 116.

According to an embodiment of the disclosure, the parameters predicted by the system 100 can also be displayed on a display device 118. The parameters may also be provided for further post processing to derive various other parameters. The parameters may also represent thermodynamic properties.

According to an embodiment of the disclosure, the system 100 is configured to overcome the factorial design of experiments needed to screen the active molecules such as drugs/cosmetics based on the predicted permeability. The system 100 also predicts the behaviors of molecules inside the SC layer at nano-scale.

According to another embodiment of the disclosure, the system 100 is also configured to predict the effect of molecular weight on the transport properties like permeability and able to predict the lateral and z direction (bilayer normal) diffusivity of molecules. Moreover, the system 100 is able to predict the partition coefficient of molecules from water to bilayer phase. The system 100 is able to predict the free energy of permeation of solutes/molecules from water to bilayer phase. The system further configured to predict the effect of hydrophobicity on the permeability.

Figure 3:
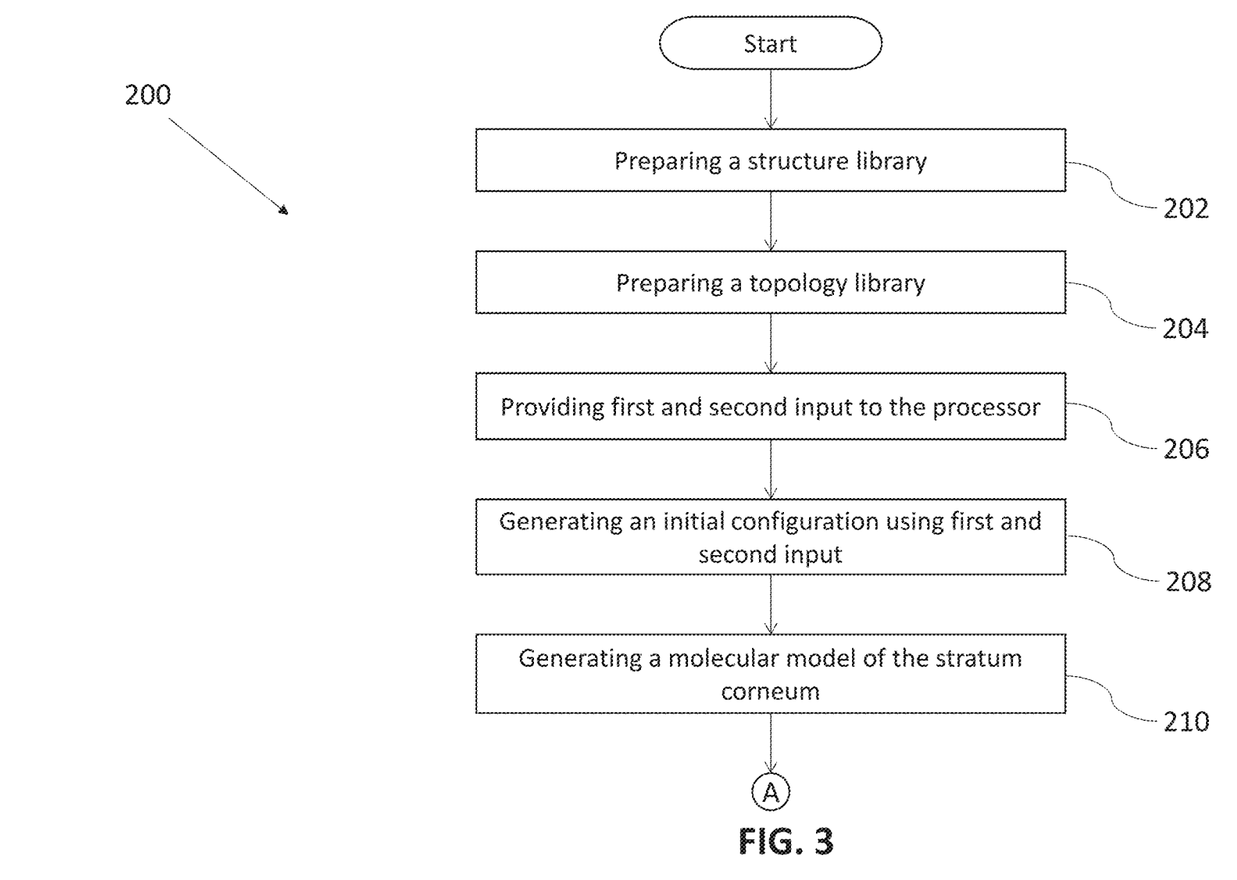
FIG. 3 is a flowchart illustrating the steps involved for testing of active molecules using simulation of skin membrane according to an embodiment of the present disclosure.

In operation, a flowchart 200 illustrates the steps involved for testing of active molecules using simulation of skin membrane as shown in FIG. 3 according to an embodiment of the disclosure. Initially at step 202, the structure library is prepared as the first input to the processor 106. It should be appreciated that the structure library may include skin lipids, stratum corneum components, biological molecules, proteins, drugs, polymers, nanoparticles, water, hydrophilic and hydrophobic molecules and solvents. At step 204, the topology library is prepared as the second input to the processor 106. The topology library includes force fields and individual molecule parameter files. At next step 206, the first input and the second input is provided to the processor 106.

At step 208, an initial configuration is generated by the processor 106 using the first input and the second input. The initial configuration generated with multiple constrained molecules. The initial configurations are prepared in such a way that in single simulation window multiple molecules (4 in current simulation) could be constrained. At next step 210, the molecular model of the stratum corneum of the skin is generated using the initial configuration prepared in the previous step. The molecular modeling develops the complex skin model at atomistic level. The molecular model employs bonded and non-bonded parameters to describe the interaction between the molecules.

At step 212, a multiple molecules in a single window constrained molecular dynamics simulation of the active molecules of the performed using the molecular model of the stratum corneum of the skin. And finally at step 214, the diffusivity of the active molecules is predicted by the processor 106 based on the simulation. At step 214, the partition coefficients of the active molecules is predicted by the processor 106 based on the simulation. And at step 216, permeability of the active molecules is predicted by the processor 106 based on the simulation.

It should be appreciated that the prediction of diffusivity, partition coefficients and the permeability of active molecules are in good qualitative agreement with experimental data according to an embodiment of the disclosure.

The stratum corneum (SC) mainly made of corneocyte (brick) and lipid matrix (mortar). The corneocyte are mostly impermeable and molecules penetrate through lipid matrix. This lipid matrix is the key determinant for the barrier functions and mainly composed of heterogeneous mixture of long chain Ceramide (CER), cholesterol (CHOL) and free fatty acid (FFA) in certain ratios. The SC made up of more than 300 different types of CER, which are classified according to the structure of head group and attached fatty acid chain length. The slight changes in the head group of CER (either position or number of OH group) can change the morphology of bilayer significantly. Atomistic simulation of molecular model of heterogeneous mixture of skin's SC layer incorporating all possible CER, FFA and CHOL is challenging and beyond the current computational capabilities. However, in order to simulate a realistic SC layer, the most abundant Ceramide, CER-NS 24:0 and free fatty acid, FFA 24:0 are chosen for molecular model. Here 24 and 0, represents the length and number of double bonds in fatty acid chain both in CER-NS and FFA respectively.

In this disclosure several independent long (~upto 30 ns) constrained MD simulations have been performed. The permeability of water, ethanol, DMSO, toluene, benzene etc. are computed in equi-molar mixture of CER, CHOL, and FFA.

According to an embodiment of the disclosure, several independent long (~upto 30 ns) constrained MD simulations were performed. In various examples the permeability of water, ethanol, DMSO, toluene and benzene are computed in equi-molar mixture of CER, CHOL and FFA. The force field parameters and the simulation setup was prepared for the simulation.

The force field parameters for the CER were taken from the Berger force field and GROMOS87 parameters. The Berger force field has been parameterized for palmitoyl-sphingomyelin (PSM) and phospholipid bilayers. The PSM's have similar structure as CER-NS except for head group geometry. The $CH_2$ and $CH_3$ groups are treated as single united atom C entity with zero partial charge and the polar hydrogen's were included explicitly and charges on polar groups were taken from earlier simulations. The Ryckaert-Bellemans dihedral potential was used for the hydrocarbon chains of FFA and CER. The parameters for FFA and CHOL were taken from the GROMOS data set. The simple point charge (SPC) model was used for water molecule.

The simulations were carried out in NVT and NPT ensemble. The temperature was controlled at 310 K by Nose-Hoover thermostat with a time constant of 5 ps and thermostat coupled separately to lipid molecules and water. Pressure was controlled at 1 bar by Parrinello-Rahman barostat with a time constant of 5 ps and compressibility of $4.5 \times 10^{-5}$ bar with semi isotropic coupling (XY and Z direction coupled separately). All the bonds in lipid and solute molecules were constrained using LINCS algorithm while SETTLE algorithm was used for water. A time step of 2 fs was used for all simulations. A cut off of 1.2 nm was used for Vander Wall and electrostatic interactions. All the systems were equilibrated for at least ~5 ns. The final 25 ns run of constrained simulation was used to calculation of constrained force and other properties. The above parameters (including barostat, thermostat and constraint algorithm etc.) are variable and can be tuned based on the system and not limited to the information given above.

Figure 4:
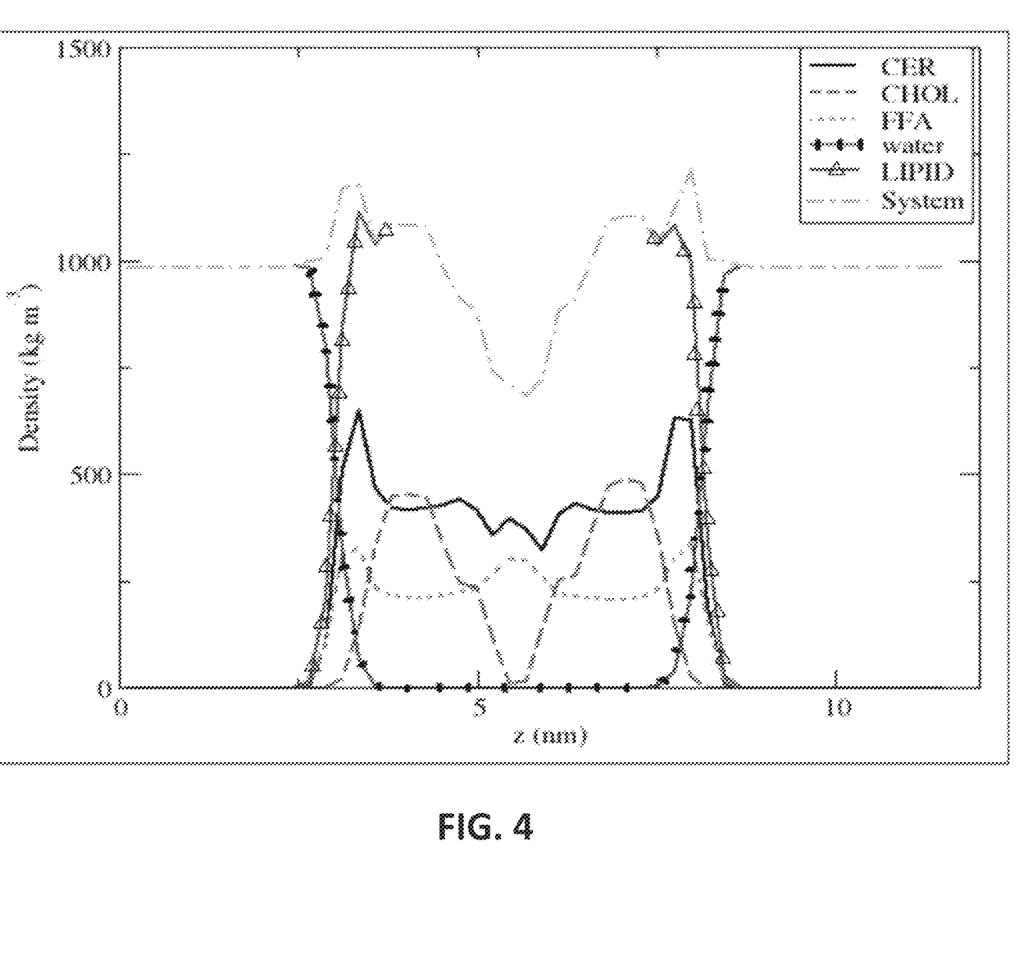
FIG. 4 is graphical representation of density of individual component of equi-molar bilayer along with bilayer normal z at 310K according to an embodiment of the disclosure.

Further initial bilayer and solute structure is also modelled. The equi-molar bilayer structure equilibrated for ~200 ns in NPT ensemble. The equi-molar bilayer is made up of 52 CER, 52 CHOL, 52 FFA and 5120 water molecules. FIG. 4 shows the density distribution of individual bilayer component along the bilayer normal at 310 K. The CHOL mostly sits in between the middle of each leaflet (z~3.5, 6.5), while there is small increase in the density of FFA and CER in the middle of bilayer (z~5.5). To sample the whole phase space of the bilayer, multiple solutes needs to be constrained at different xy and z plane. To do this efficiently, the models were prepared in the following manner. It must be noted that the proposed protocol is not limited to the times and sizes mentioned above.

The reaction coordinate was chosen to be membrane normal z, where z=0 nm is correspond to the center of mass (COM) of the bilayer. For each of the setup, four molecules placed manually at different xy plane and z distance of ~4.8 nm from the COM of the bilayer. Overlapped water molecules with solutes were removed and the set up was then energy minimized. Each set up was then equilibrated in NPT ensemble for another 20 ns by keeping solute molecules fixed at their positions. These equilibrated structures were further used for the preparation of the initial configuration of constrained simulations. Solutes were pulled slowly with different velocity towards the center of bilayer. The time step for this run was kept at 1 fs. As the z distance between the center of mass (COM) of the lipid and solute molecule changes by 0.2 nm, the configuration was stored. In each window, four solutes were constrained at different z and xy position. Total 24 windows were generated using the above procedure. These windows span the whole space from the bulk water from upper leaflet to the middle of the bilayer. To stop the interaction in between the solutes which are in the same window, the minimum z distances were kept as 1.2 nm (cut off for vdW and coulomb). It must be noted that the proposed protocol is not limited to the times and sizes mentioned above.

The stored equidistance configuration was further run for 30 ns out of which first 5 ns simulation was discarded as an equilibration run. The distance between the COM of solute and COM of bilayer was constrained in z direction while solute was free to move in lateral direction. The configuration was stored at every 1 ps and constrained force was stored at every 10 fs. Last 25 ns runs of each simulation were used to calculate diffusion and potential of mean force. To improve the statistical accuracy of sampling, each solute was constrained at four different xy plane for a given z coordinate. Averages of these four simulations for each solute are presented here. It was assumed that bilayer is symmetric and result from the one side of bilayer will be the mirror image of the result of other side. It must be noted that the proposed protocol is not limited to the times and sizes mentioned above.

And finally potential of mean force and diffusivity is predicted according to an embodiment of the disclosure. The homogenous solubility diffusion model is generally used for the calculation of passive permeability of solutes through membranes. According to this model the solute first dissolves into the membrane, then diffuses through the membrane interior, and finally dissolves again in the outer surrounding medium. The permeability for this model is given by $$P = \frac{KD}{d}$$

Where p is the permeability of the molecules across the bilayer, K is the solute partition function from aqueous to organic phase, D is the diffusion coefficient of solute and d is the thickness of the bilayer. It has been shown previously that solute size and composition changes the permeability many folds as well as local partition function governs the solute permeability.

Molecular dynamics simulation provides a way to calculate $K(z)$ and $D(z)$ along the bilayer normal z. A nonhomogeneous solubility diffusion model was adopted to compute the diffusivity, partition function, potential of mean force (PMF) and permeability.

The permeability for a symmetric bilayer system which has normal in z direction can be given by $$\frac{1}{P} = \int_{-d2}^{d2} \frac{1}{K(z)D(z)} dz$$

Where P is the permeability, d is thickness of the bilayer. $K(z)$ and $D(z)$ is partition function and diffusion coefficient at a given z position from the center of bilayer, which are calculated using following equation $$D(z) = \frac{(RT)^2}{\int_0^\infty <(\Delta F(z,t) \Delta F(z,0))> dt}$$

$$K(z) = \exp\left(\frac{-\Delta G(z)}{kT}\right)$$

$$\Delta F(z,t) = F(z,t) - <F(z,t)>$$

$$\frac{\partial \Delta G(z)}{\partial z} = -\Delta F(z,t)$$

Where R is gas constant, T is temperature, $F(z,t)$ is constrained force on solute at a given z and G is potential of mean force.

Based on the above mentioned simulations following results were observed:

Free energy of permeation of water in the center of the bilayer (z~0) is ~23 kJ/mol which is comparable to the experimentally observed free energy (25 kJ/mol) of water solvation in hexadecane at 323 K.

The free energy of permeation of DMSO and ethanol are lower (–ve) from the bulk at the interface because of presence of partial charges on head groups.

The free energy of permeation of benzene and toluene are higher from the bulk at the interface because of presence of partial charges on head groups.

Free energy of permeation of DMSO and ethanol near the interface of water and lipid head group was found to be ~–10.0 kJ/mol and –6.0 kJ/mol which supports the fact that DMSO (log P=–1.35) is more hydrophilic than ethanol (log P=–0.31).

The partition coefficient K is an order of magnitude higher near the interface for DMSO as compare to ethanol.

The partition coefficient K both toluene and benzene are higher in the alkane chain region, while, it is higher at the interface for water, DMSO and ethanol.

The diffusion coefficient in bulk water for DMSO and ethanol is $(4.02+-0.2) \times 10^{-5}$ cm$^2$/s and $(4.62+-0.5) \times 10^{-5}$ cm$^2$/s.

Diffusion inside the bilayer decreased by almost an order as compare to the bulk value for all solutes.

The calculated permeability of DMSO and Ethanol at temperature of 310 K was found to be ~$4.789 \times 10^{-6}$ cm/s and $6.952 \times 10^{-6}$ cm/s respectively.

The overall resistance to permeation R (z) profile follows the free energy profile G (z) which shows that permeability mostly depends upon the free energy barrier.

The partition coefficient K (z) profile complimentary to free energy profile.

The resistance to permeation (R) was higher for DMSO at the bilayer center because of its highly hydrophilic nature.

The permeation resistance (R) was higher for the benzene and toluene at the interface, while it is higher in the alkane chain for water, DMSO and ethanol.

The computed and experimental permeability follow different trends for the hydrophobic and hydrophilic permeates.

Figure 5:
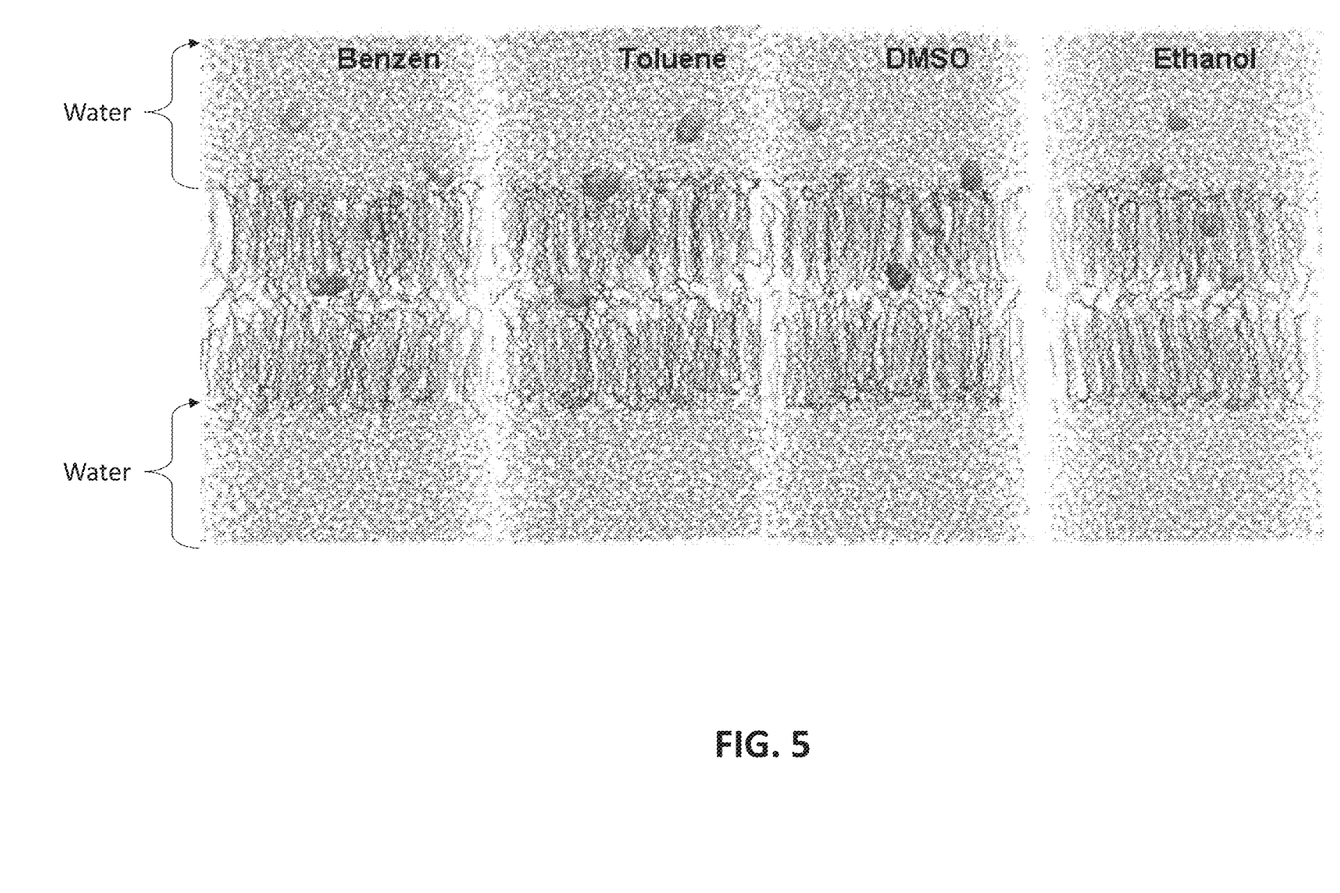
FIG. 5 shows a side view of simulation snapshot of multiple molecules constrained in single window according to an embodiment of the disclosure.
Figure 6:
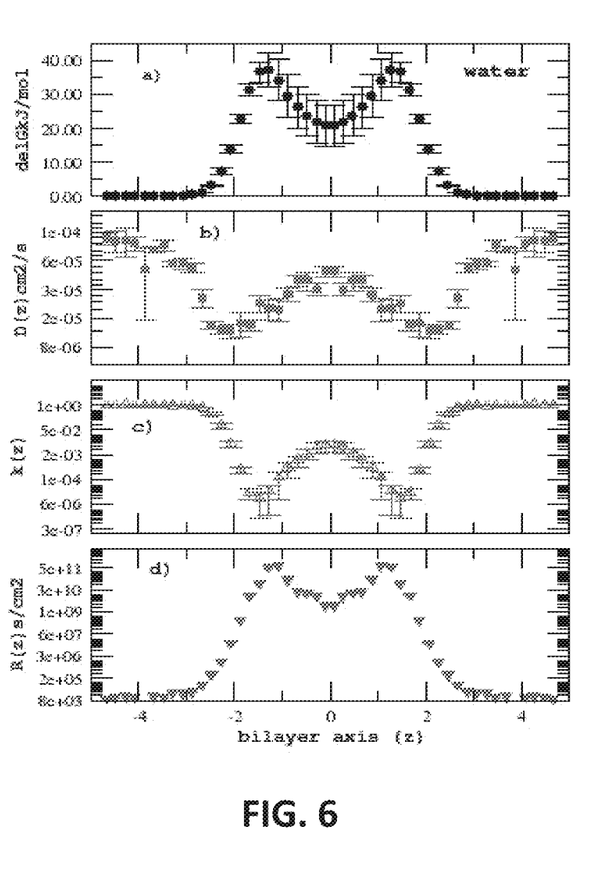
FIG. 6 shows a graphical representation of free energy of permeation (potential of mean force), local diffusion coefficient, local partition function and local resistance of water permeation through mixed CER:CHOL:FFA (1:1:1) bilayer obtained from constrained MD simulations according to an embodiment of the disclosure.
Figure 7:
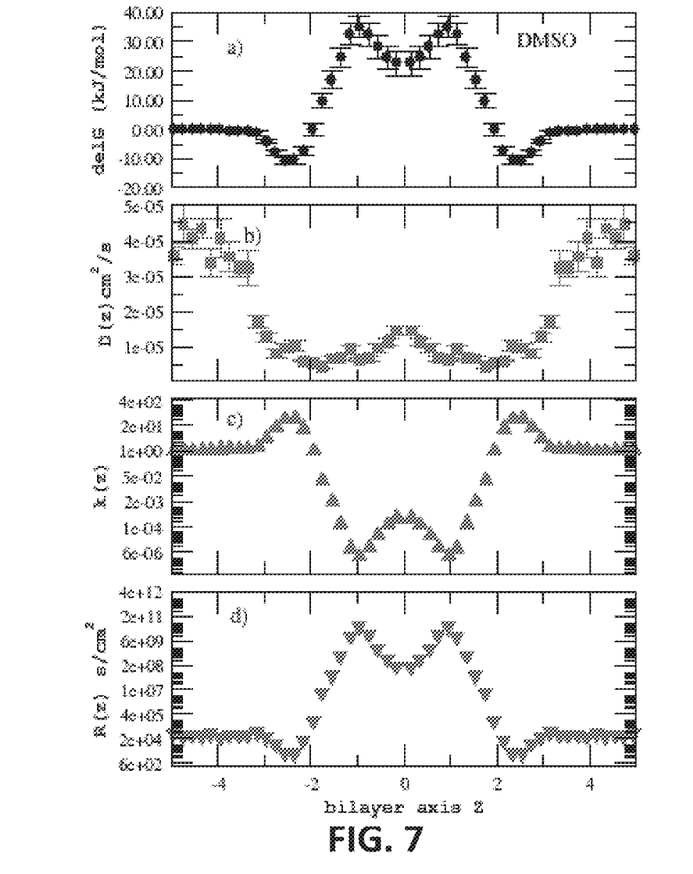
FIG. 7 shows a graphical representation of free energy of permeation (potential of mean force), local diffusion coefficient, local partition function and local resistance of DMSO permeation through mixed CER:CHOL:FFA (1:1:1) bilayer obtained from constrained MD simulations according to an embodiment of the disclosure.
Figure 8:
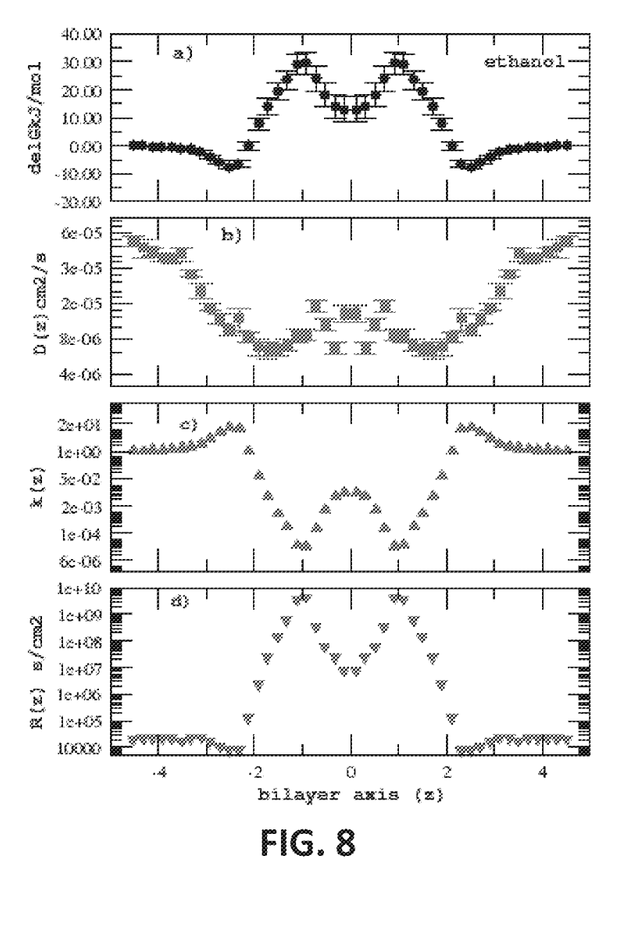
FIG. 8 shows a graphical representation of free energy of permeation (potential of mean force), local diffusion coefficient, local partition function and local resistance of ethanol permeation through mixed CER:CHOL:FFA (1:1:1) bilayer obtained from constrained MD simulations according to an embodiment of the disclosure.
Figure 9:
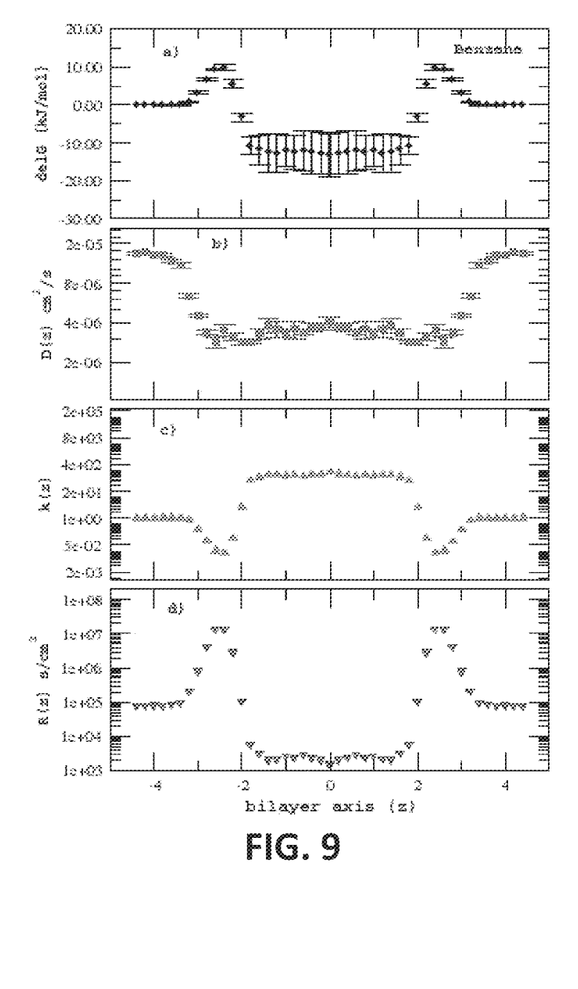
FIG. 9 shows a graphical representation of free energy of permeation (potential of mean force), local diffusion coefficient, local partition function and local resistance of benzene permeation through mixed CER:CHOL:FFA (1:1:1) bilayer obtained from constrained MD simulations according to an embodiment of the disclosure.
Figure 10:
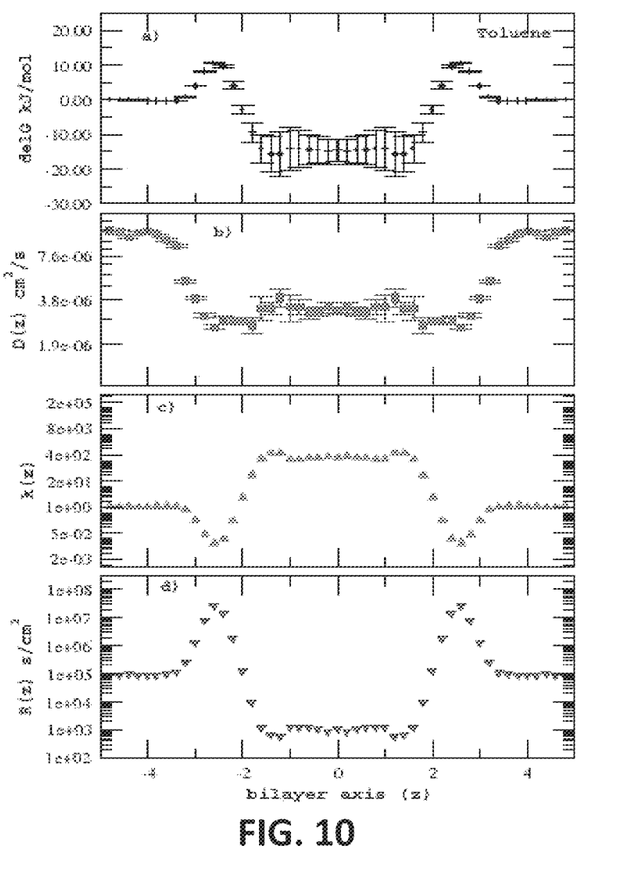
FIG. 10 shows a graphical representation of free energy of permeation (potential of mean force), local diffusion coefficient, local partition function and local resistance of toluene permeation through mixed CER:CHOL:FFA (1:1:1) bilayer obtained from constrained MD simulations according to an embodiment of the disclosure.
Figure 11:
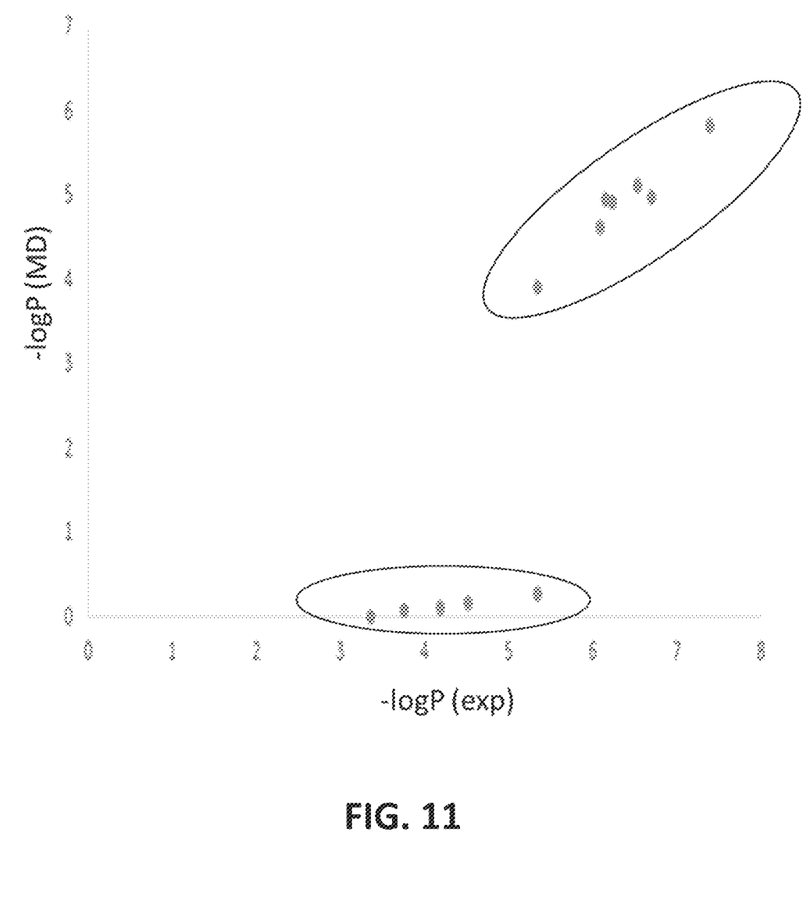
FIG. 11 shows a comparison of experimental permeability with the permeability of hydrophobic and hydrophilic permeates through mixed CER:CHOL:FFA (1:1:1) bilayer obtained from constrained MD simulations according to an embodiment of the disclosure.

FIG. 5 shows a side view of simulation snapshot of multiple molecules constrained in single window. The molecules are separated at least 1.2 nm in z direction from each other. Initial configurations of constrained molecules at different xy and z position in one of the window. Based on the above experiments and results, a graphical representation of free energy of permeation (potential of mean force), local diffusion coefficient, local partition function and local resistance of various active molecules permeation through mixed CER:CHOL:FFA (1:1:1) bilayer obtained from constrained MD simulations is shown in FIG. 6 for water, FIG. 7 for DMSO, FIG. 8 for ethanol, FIG. 9 for benzene and FIG. 10 for toluene. Further, FIG. 11 shows a comparison of experimental permeability with the permeability of hydrophobic and hydrophilic permeates through mixed CER:CHOL:FFA (1:1:1) bilayer obtained from constrained MD simulations.

The written description describes the subject matter herein to enable any person skilled in the art to make and use the embodiments. The scope of the subject matter embodiments is defined by the claims and may include other modifications that occur to those skilled in the art. Such other modifications are intended to be within the scope of the claims if they have similar elements that do not differ from the literal language of the claims or if they include equivalent elements with insubstantial differences from the literal language of the claims. The embodiment, thus provides the system and method for testing of active molecules using simulation of skin membrane It is, however to be understood that the scope of the protection is extended to such a program and in addition to a computer-readable means having a message therein; such computer-readable storage means contain program-code means for implementation of one or more steps of the method, when the program runs on a server or mobile device or any suitable programmable device. The hardware device can be any kind of device which can be programmed including e.g. any kind of computer like a server or a personal computer, or the like, or any combination thereof. The device may also include means which could be e.g. hardware means like e.g. an application-specific integrated circuit (ASIC), a field-programmable gate array (FPGA), or a combination of hardware and software means, e.g. an ASIC and an FPGA, or at least one microprocessor and at least one memory with software modules located therein. Thus, the means can include both hardware means and software means. The method embodiments described herein could be implemented in hardware and software. The device may also include software means. Alternatively, the embodiments may be implemented on different hardware devices, e.g. using a plurality of CPUs.

The embodiments herein can comprise hardware and software elements. The embodiments that are implemented in software include but are not limited to, firmware, resident software, microcode, etc. The functions performed by various modules described herein may be implemented in other modules or combinations of other modules. For the purposes of this description, a computer-usable or computer readable medium can be any apparatus that can comprise, store, communicate, propagate, or transport the program for use by or in connection with the instruction execution system, apparatus, or device.

The medium can be an electronic, magnetic, optical, electromagnetic, infrared, or semiconductor system (or apparatus or device) or a propagation medium. Examples of a computer-readable medium include a semiconductor or solid state memory, magnetic tape, a removable computer diskette, a random access memory (RAM), a read-only memory (ROM), a rigid magnetic disk and an optical disk. Current examples of optical disks include compact disk-read only memory (CD-ROM), compact disk-read/write (CD-R/W) and DVD.

A data processing system suitable for storing and/or executing program code will include at least one processor coupled directly or indirectly to memory elements through a system bus. The memory elements can include local memory employed during actual execution of the program code, bulk storage, and cache memories which provide temporary storage of at least some program code in order to reduce the number of times code must be retrieved from bulk storage during execution.

Input/output (I/O) devices (including but not limited to keyboards, displays, pointing devices, etc.) can be coupled to the system either directly or through intervening I/O controllers. Network adapters may also be coupled to the system to enable the data processing system to become coupled to other data processing systems or remote printers or storage devices through intervening private or public networks. Modems, cable modem and Ethernet cards are just a few of the currently available types of network adapters.

A representative hardware environment for practicing the embodiments may include a hardware configuration of an information handling/computer system in accordance with the embodiments herein. The system herein comprises at least one processor or central processing unit (CPU). The CPUs are interconnected via system bus to various devices such as a random access memory (RAM), read-only memory (ROM), and an input/output (I/O) adapter. The I/O adapter can connect to peripheral devices, such as disk units and tape drives, or other program storage devices that are readable by the system. The system can read the inventive instructions on the program storage devices and follow these instructions to execute the methodology of the embodiments herein.

The system further includes a user interface adapter that connects a keyboard, mouse, speaker, microphone, and/or other user interface devices such as a touch screen device (not shown) to the bus to gather user input. Additionally, a communication adapter connects the bus to a data processing network, and a display adapter connects the bus to a display device which may be embodied as an output device such as a monitor, printer, or transmitter, for example.

The preceding description has been presented with reference to various embodiments. Persons having ordinary skill in the art and technology to which this application pertains will appreciate that alterations and changes in the described structures and methods of operation can be practiced without meaningfully departing from the principle, spirit and scope.

What is claimed is:

1. A method for testing of active molecules using simulation of skin membrane, the method comprising a processor implemented steps of:
preparing a structure library, wherein the structure library is a first input;
preparing a topology library, wherein the topology library is a second input;
providing the first input and the second input to the processor;
generating an initial configuration by the processor using the first input and the second input;
generating, by the processor, a molecular model of the stratum corneum of the skin using the initial configuration;
constraining, by the processor, multiple molecules in a single window molecular dynamics simulation of the active molecules using the molecular model of the stratum corneum of the skin;
predicting, by the processor, diffusivity of the active molecules based on the simulation;
predicting, by the processor, partition coefficients of the active molecules based on the simulation; and
predicting, by the processor, permeability of the active molecules based on the simulation.

2. The method of claim 1 further include the step of visualizing the diffusivity, partition coefficients profiles and the permeability of the active molecules on a display device.

3. The method of claim 1, wherein the diffusivity and the partition coefficients of the active molecules is predicted along the bilayer normal.

4. The method of claim 1, wherein the molecular model employs bonded and non-bonded parameters to describe the interaction between the active molecules.

5. The method of claim 1, wherein the prediction of the permeability further comprises calculation of amount of force required for constrained in the simulation.

6. The method of claim 1 wherein the molecular model of stratum corneum consists of lipid bilayers and corneocytes.

7. The method of claim 1, wherein the structure library includes stratum corneum components, active molecules, proteins, drugs, polymers, nanoparticles and solvents.

8. The method of claim 1, wherein the topology library includes force fields and individual molecule parameter files.

9. A system for testing of active molecules using simulation of skin membrane, the system comprising:
- a user interface for providing a structure library as a first input and a topology library as a second input;
- a memory; and
- a processor in communication with the memory, the processor comprising,
  - a model generation module for generating a molecular model of the lipid matrix of the stratum corneum of the skin,
  - a simulation module for constraining multiple molecules in a single window molecular dynamics simulation on the active molecules using the molecular model of the stratum corneum of the skin,
  - a diffusivity calculation module for predicting diffusivity of the active molecules based on the simulation;
  - a partition coefficient prediction module for predicting partition coefficients of the active molecules based on the simulation, and
  - a permeability prediction module for predicting permeability of the active molecules based on the simulation.

10. A non-transitory computer-readable medium having embodied thereon a computer program for testing of active molecules using simulation of skin membrane, the method comprising:
- preparing a structure library, wherein the structure library is a first input;
- preparing a topology library, wherein the topology library is a second input;
- providing the first input and the second input to the processor;
- generating an initial configuration by the processor using the first input and the second input;
- generating, by the processor, a molecular model of the stratum corneum of the skin using the initial configuration;
- constraining, by the processor, multiple molecules in a single window molecular dynamics simulation of the active molecules using the molecular model of the stratum corneum of the skin;
- predicting, by the processor, diffusivity of the active molecules based on the simulation;
- predicting, by the processor, partition coefficients of the active molecules based on the simulation; and
- predicting, by the processor, permeability of the active molecules based on the simulation.

* * * * *